(12) United States Patent
Patel et al.

(10) Patent No.: US 9,133,196 B2
(45) Date of Patent: Sep. 15, 2015

(54) PROCESS FOR THE PREPARATION OF ACEBROPHYLLINE

(71) Applicant: AMI LIFESCIENCES PVT. LTD., Baroda, Gujarat (IN)

(72) Inventors: Kalpesh Ravajibhai Patel, Gujarat (IN); Virendra Haridasbhai Thakrar, Gujarat (IN); Dipti Kishorbhai Dodiya, Gujarat (IN); Sharad Kanabhai Solanki, Gujarat (IN); Kinchit Jitendrakumar Shah, Gujarat (IN)

(73) Assignee: AMI LIFESCIENCES PVT. LTD., Gujarat, Baroda (IN)

( * ) Notice: Subject to any disclaimer, the term of this patent is extended or adjusted under 35 U.S.C. 154(b) by 0 days.

(21) Appl. No.: 14/352,168

(22) PCT Filed: Feb. 7, 2013

(86) PCT No.: PCT/IN2013/000082
§ 371 (c)(1),
(2) Date: Apr. 16, 2014

(87) PCT Pub. No.: WO2014/080413
PCT Pub. Date: May 30, 2014

(65) Prior Publication Data
US 2015/0218166 A1 Aug. 6, 2015

(30) Foreign Application Priority Data

Nov. 22, 2012 (IN) .......................... 3341/MUM/2012

(51) Int. Cl.
*C07D 473/08* (2006.01)
*C07C 213/08* (2006.01)

(52) U.S. Cl.
CPC ............ *C07D 473/08* (2013.01); *C07C 213/08* (2013.01)

(58) Field of Classification Search
USPC ........................................................ 544/271
See application file for complete search history.

(56) References Cited

FOREIGN PATENT DOCUMENTS

| CN | 101407517 | 4/2009 |
| WO | WO 2012/123502 | 9/2012 |

OTHER PUBLICATIONS

Written Opinion of the International Searching Authority for PCT/IN2013/000082, 2013.
Foppoli et al., "Solid-State Chemistry of Ambroxol Theophylline-7-Acetate", Journal of Pharmaceutical Sciences, vol. 96, pp. 1139-1146 (2007).

*Primary Examiner* — Kristin Vajda
(74) *Attorney, Agent, or Firm* — Nixon & Vanderhye P.C.

(57) ABSTRACT

The present invention relates to an improved process for preparing Acebrophylline comprising preparing a reaction mixture of theophylline-7-acetate and ambroxol base in a non-polar solvent; heating said reaction mixture at a suitable temperature; and isolating Acebrophylline by filtration. The yield of Acebrophylline is between 95-98% with a purity of 99%.

17 Claims, No Drawings

PROCESS FOR THE PREPARATION OF ACEBROPHYLLINE

This application is the U.S. national phase of International Application No. PCT/IN2013/000082 filed 7 Feb. 2013 which designated the U.S. and claims priority to IN 3341/MUM/2012 filed 22 Nov. 2012, the entire contents of each of which are hereby incorporated by reference.

FIELD OF THE INVENTION

The present invention relates to an improved process for preparing Acebrophylline. The invention provides a process for preparing Acebrophylline from theophylline-7-acetic acid and ambroxol base using non-polar solvent.

BACKGROUND OF THE INVENTION

Acebrophylline is a mucolytic bronchodilator used for the treatment of Chronic Obstructive Pulmonary Disorders (COPD). Acebrophylline act like an airway mucus regulator with Anti-inflammatory action. A number of processes are known for preparing Acebrophylline.

DE3425007 describes preparation of Acebrophylline involving reaction of ambroxol base and theophylline-7-acetic acid in a polar aprotic solvent followed by precipitation using ethyl acetate.

However, this process is disadvantageous and not suitable for large scale commercial preparation as it requires very high volume of ethyl acetate for precipitation and separation. The yield obtained by this method is only 85% of the theoretical yield.

BR2001003368 describes preparation of Acebrophylline by neutralization of methanolic solutions of ambroxol base and theophylline-7-acetic acid in the presence of activated carbon and alumina during reflux.

The use and handling of alumina in bulk at the production level is problematic. Further, the product separation has to be achieved by adding ethanol; followed by removing mixture of methanol and ethanol by distillation.

CN101407517B describes preparation of Acebrophylline employing theophylline-7-acetic acid and ambroxol base in 1:1.49-1.69 weight proportion using mixture of water with ethanol or ethanol as a solvent.

The process uses excess of ambroxol base which is not commercially feasible. Also, the yield of crude product obtained is only 77% of the theoretical yield and the crude product needs to be re-crystallized. Further, isolation of the product is effected by the distillation followed by filtration.

The processes for the preparation of Acebrophylline known in the art suffers from several drawbacks like, lower yields, use of higher amount of reactants, higher volume of solvents, longer reaction time and cumbersome product isolation procedures. Therefore, improved methods for the industrial scale preparation of Acebrophylline are desirable which can overcome the above mentioned drawbacks.

OBJECT OF THE INVENTION

Accordingly, an object of the present invention is to provide a simple, cost effective and an efficient process for the production of Acebrophylline without compromising the quality and yield of the Acebrophylline.

SUMMARY OF THE INVENTION

The present invention provides an improved process for the preparation of Acebrophylline. In particular, the invention provides a process for the preparation of Acebrophylline using a non-polar solvent.

The process for preparing Acebrophylline comprises preparing a reaction mixture of theophylline-7-acetic acid and ambroxol base in a non-polar solvent; heating said reaction mixture at a suitable temperature and isolating Acebrophylline by filtration.

In one embodiment, the theophylline-7-acetic acid and ambroxol base are used in an equimolar amount.

In another embodiment, the ratio of ambroxol base and total amount of non-polar solvent employed to prepare the reaction mixture is 1:9 to 1:18 (w/v). In another embodiment, the ratio of ambroxol base and total amount of non-polar solvent in the reaction mixture is 1:10 to 1:13 (w/v).

In another embodiment, the non-polar solvent is selected from aromatic hydrocarbons, halogenated hydrocarbons or a mixture thereof. The aromatic hydrocarbon used is selected form benzene, toluene, xylenes and ethylbenzene. The halogenated hydrocarbon is selected from carbon tetrachloride and chloroform.

In another embodiment, the non-polar solvent used is toluene, carbon tetrachloride or chloroform. In another embodiment, the non-polar solvent used is toluene.

In yet another embodiment, the process comprises heating the reaction mixture at a temperature between 60-110° C.

In another embodiment, the heating is done for a period of 25-35 minutes.

In another embodiment, the reaction mixture is allowed to cool at a room temperature.

In an embodiment, the Acebrophylline product is separated by filtration. The process of filtration used is suction (vacuum) filtration.

In still another embodiment, the invention provides a process for preparing Acebrophylline, the process comprises the steps of heating the reaction mixture containing equimolar amounts of theophylline-7-acetic acid and ambroxol base in toluene at a temperature of 100-105° C. for 25-30 minutes and isolating the Acebrophylline by filtration.

In yet another embodiment the invention provides a process for preparing Acebrophylline, the process comprises the steps of heating the reaction mixture containing equimolar amounts of theophylline-7-acetic acid and ambroxol base in carbon tetrachloride at a temperature of 70-75° C. for 30-35 minutes and isolating the Acebrophylline by filtration.

In yet another embodiment the invention provides a process for preparing Acebrophylline, the process comprises the steps of heating the reaction mixture containing equimolar amounts of theophylline-7-acetic acid and ambroxol base in chloroform at a temperature of 60-65° C. for 25-30 minutes and isolating the Acebrophylline by filtration.

In another embodiment, the yield of Acebrophylline obtained is 95-98% of the theoretical yield. In another embodiment, the yield of Acebrophylline obtained is 154-159% of the weight of ambroxol base.

In another embodiment, the purity of Acebrophylline obtained is more than 99%.

DETAILED DESCRIPTION OF THE INVENTION

The present invention relates to an improved process for preparing Acebrophylline. In particular, the invention provides a process for preparing Acebrophylline in a non-polar solvent.

Chemically Acebrophylline is 1,2,3,6-tetrahydro-1,3-dimethyl-2,6-dioxo-7H-Purine-7-acetic acid with trans-4-[[(2-amino-3,5-dibromophenyl)methyl]amino]cyclohexanol (1:1).

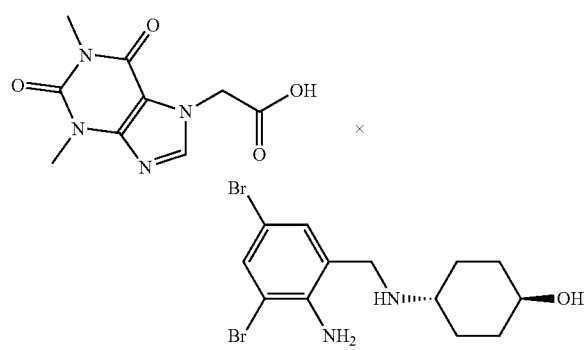

The processes for the preparation of Acebrophylline known in the art employ higher amount of organic solvents and ambroxol base and suffered from various drawbacks as discussed above. The present invention provides an improved process for preparing Acebrophylline in a non-polar solvent.

The process involves preparing a reaction mixture of theophylline-7-acetic acid and ambroxol base in a non-polar solvent. The theophylline-7-acetic acid and ambroxol base are used in an equimolar amount. The ratio of ambroxol base and total amount of non-polar solvent employed to prepare reaction mixture is 1:9 to 1:18 (w/v). In another embodiment, the ratio of ambroxol base to total amount of non-polar solvent in the reaction mixture, is 1:10 to 1:13 (w/v).

The non-polar solvents used are selected from aromatic hydrocarbons, halogenated hydrocarbons or a mixture thereof. The aromatic hydrocarbons used in the present process include but not limited to, benzene, toluene, xylenes and ethylbenzene. The halogenated hydrocarbons used in the present process include but not limited to, carbon tetrachloride and chloroform. In an embodiment, the non-polar solvent used is toluene. In another embodiment, the non-polar solvent used is carbon tetrachloride. In still another embodiment, the non-polar solvent used is chloroform.

Theophylline-7-acetic acid is prepared by the reaction of theophylline with monochloroacetic acid at 85-90° C. in the presence of sodium carbonate using water as a solvent. Theophylline-7-acetic acid and non-polar solvent are charged in a round bottom flask wherein the ratio of theophylline-7-acetic acid and the amount of non-polar solvent charged is 1:4 to 1:8 (w/v). In another embodiment, the ratio of theophylline-7-acetic-acid and the amount of non-polar solvent charged is 1:5 to 1:7 (w/v). The resulting mass is heated to a temperature between 60-80° C.

Ambroxol base may be prepared using the process based on ES8904106 and ES8602601. A solution of ambroxol base is prepared in a non-polar solvent wherein the ratio of ambroxol base and the amount of non-polar solvent employed is 1:5 to 1:10 (w/v). In another embodiment, the ratio of ambroxol base and the amount of non-polar solvent employed is 1:5 to 1:8 (w/v). The solution is prepared by stirring ambroxol base with a non-polar solvent at room temperature or by heating mixture of ambroxol base and non-polar solvent at a temperature between 45-65° C.

The solution of ambroxol base in non-polar solvent is added to the flask containing theophylline-7-acetic acid and non-polar solvent under stirring while maintaining the temperature between 60-85° C. The addition time is 2-3 minutes. The reaction mixture is heated at the temperature between 60-105° C. with continuous stirring for 25-35 minutes. The reaction mixture is allowed to cool to the room temperature. A solid product is formed. This solid product is separated by filtration. The product is washed with the small amount of non-polar solvent and dried. The yield of Acebrophylline obtained is 95-98% of the theoretical yield. The yield of Acebrophylline is 154-159% of the weight of ambroxol base. The purity of Acebrophylline thus obtained as measured by HPLC is more than 99%.

The present invention provides a process for preparing Acebrophylline that is advantageous over the prior art processes in terms of higher yield (95-98%), shorter reaction time, use of much lower volume of solvents and easy isolation/separation of product. A comparison has been made between the processes for the preparation of Acebrophylline disclosed in BR2001003368A, CN101407517B, DE3425007C2 and the present process. The observations are shown in the table below:

| Patent No. | Example No. | Quantity of Ambroxol Base | Quantity of TAA# | Temp. °C. | Solvent | Solvent Volume | Reaction Time | % Yield | Isolation Procedure |
|---|---|---|---|---|---|---|---|---|---|
| BR2001003368A* | N.A. | N.A. | N.A. | 0-50 | Methanol | N.A. | 10-30 Min. | N.A. | Distillation |
| CN101407517B | 1 | 7.93 g | 5 g | 60-65 | Water + Ethanol | 200 + 60 mL | 40-50 Min. | 77.39 (crude) | Vacuum distillation followed by filtration |
| | 2 | | | | Ethanol | 240 mL | | | |
| DE3425007C2 | 1 | 378.1 g | 238.2 g | 40 | DMF (+Ethyl acetate) | 2 L + 20 L | N.A. | 85 (pure) | Precipitation by anti-solvent |
| Present Invention | 1 | 20.0 g | 12.6 g | 100-105 | Toluene | 260 mL | 25-35 Min. | 95-98 (pure) | Filtration of separated solid |
| | 2 | | | 70-75 | CCl$_4$ | 200 mL | | | |
| | 3 | | | 60-65 | Chloroform | 200 mL | | | |
| | 4 | 378.1 g | 238.2 g | 100-105 | Toluene | 4.9 L | | | |

*BR2001003368A employs additional reagents viz. activated carbon and alumina during the reaction.
N.A. = Information not available.
TAA = Theophylline-7-acetic-acid The preferred embodiments of the invention are illustrated by way of the following working examples and should not be construed to limit the scope of the invention.

Example 1

The mixture of ambroxol base (20.0 g, 0.052 moles) and toluene (160 ml) was heated at 60-65° C. for 1-2 minutes to prepare a clear solution. Toluene (100 ml) and theophylline-7-acetic acid (12.6 g, 0.052 moles) were charged in a round bottom flask and heated at 75 to 80° C. To this flask, the prepared solution of ambroxol base in toluene was added under stirring while maintaining the temperature between 75-80° C. during 2-3 minutes. The resulting reaction mixture was stirred at 100-105° C. for 25-30 minutes. The reaction mixture was allowed to cool to room temperature. The separated solid product was filtered and washed with toluene and dried. The yield of Acebrophylline obtained was 98.2%.

Example 2

The mixture of ambroxol base (20.0 g, 0.052 moles) and carbon tetrachloride (100 ml) was heated at 45-50° C. for 1-2 minutes to prepare a clear solution. Carbon tetrachloride (100 ml) and theophylline-7-acetic acid (12.6 g, 0.052 moles) were charged in a round bottom flask and heated at 60 to 65° C. To this flask, the prepared solution of ambroxol base in carbon tetrachloride was added under stirring while maintaining the temperature between 60-65° C. during 2-3 minutes. The resulting reaction mixture was stirred at 70-75° C. for 30-35 minutes. The reaction mixture was allowed to cool to room temperature. The separated solid product was filtered and washed with carbon tetrachloride and dried. The yield of Acebrophylline obtained was 95.2%.

Example 3

Ambroxol base (20.0 g, 0.052 moles) was dissolved in chloroform (100 ml) at room temperature. Chloroform (100 ml) and theophylline-7-acetic acid (12.6 g, 0.052 moles) were charged in a round bottom flask and heated at 60 to 65° C. To this flask, the prepared solution of ambroxol base in chloroform was added under stirring while maintaining the temperature between 60-65° C. during 2-3 minutes. The resulting reaction mixture was stirred at 60-65° C. for 25-30 minutes. The reaction mixture was allowed to cool to room temperature. The separated solid product was filtered and washed with chloroform and dried. The yield of Acebrophylline obtained was 97.8%.

Example 4

The mixture of ambroxol base (378.1 g, 1 mole) and toluene (3000 ml) was heated at 60-65° C. for 1-2 minutes to prepare a clear solution. Toluene (1900 ml) and theophylline-7-acetic acid (238.2 g, 1 mole) were charged in a round bottom flask and heated at 75 to 80° C. To this flask, the prepared solution of ambroxol base in toluene was added under stirring while maintaining the temperature between 75-80° C. during 2-3 minutes. The resulting reaction mixture was stirred at 100-105° C. for 25-30 minutes. The reaction mixture was allowed to cool to room temperature. The separated solid product was filtered and washed with toluene and dried. The yield of Acebrophylline obtained was 98%.

We claim:
1. A process for preparing Acebrophylline comprising:
(a) preparing a reaction mixture of theophylline-7-acetic acid and ambroxol base in non-polar solvent;
(b) heating said reaction mixture at a suitable temperature; and
(c) isolating Acebrophylline by filtration.
2. The process of claim 1, wherein theophylline-7-acetic acid and ambroxol base are used in an equimolar amount.
3. The process of claim 1, wherein, in the step (a), the ratio of ambroxol base and total amount of non-polar solvent employed to prepare the reaction mixture is 1:9 to 1:18 (w/v).
4. The process of claim 3, wherein the ratio of ambroxol base and total amount of non-polar solvent employed to prepare the reaction mixture is 1:10 to 1:13 (w/v).
5. The process of claim 1, wherein the non-polar solvent is selected from aromatic hydrocarbons, halogenated hydrocarbons or mixtures thereof.
6. The process of claim 5, wherein the aromatic hydrocarbon is selected from benzene, toluene, xylenes or ethylbenzene; and the halogenated hydrocarbon is selected from chloroform or carbon tetrachloride.
7. The process of claim 1, wherein the non-polar solvent used is preferably toluene, chloroform, carbon tetrachloride or mixtures thereof.
8. The process of claim 1, wherein the non-polar solvent used is toluene.
9. The process of claim 1, wherein the heating is done at a temperature in the range of 60-110° C. for 25-35 min.
10. A process for preparing Acebrophylline comprising the steps of:
(a) preparing a reaction mixture of theophylline-7-acetic acid and ambroxol base in toluene;
(b) heating the reaction mixture at a temperature of 100-105° C. for 25-30 minutes; and
(c) isolating Acebrophylline by filtration.
11. The process of claim 10, wherein theophylline-7-acetic acid and ambroxol base are used in an equimolar amount.
12. The process of claim 10, wherein, in the step (a), the ratio of ambroxol base and total amount of toluene employed to prepare the reaction mixture is 1:9 to 1:18 (w/v).
13. The process of claim 12, wherein the ratio of ambroxol base and total amount of toluene employed to prepare the reaction mixture is 1:10 to 1:13 (w/v).
14. A process for preparing Acebrophylline comprising the steps of:
(a) preparing a reaction mixture of theophylline-7-acetic acid and ambroxol base in chloroform;
(b) heating the reaction mixture at a temperature of 60-65° C. for 25-30 minutes; and
(c) isolating the Acebrophylline by filtration.
15. The process of claim 14, wherein theophylline-7-acetic acid and ambroxol base are used in an equimolar amount.
16. The process of claim 14, wherein, in the step (a), the ratio of ambroxol base and total amount of chloroform employed to prepare the reaction mixture is 1:9 to 1:18 (w/v).
17. The process of claim 16, wherein the ratio of ambroxol base and total amount of chloroform employed to prepare the reaction mixture is 1:10 to 1:13 (w/v).

* * * * *